(12) United States Patent
Mathias et al.

(10) Patent No.: US 6,669,905 B1
(45) Date of Patent: Dec. 30, 2003

(54) SYSTEMS AND METHODS FOR COLLECTING PLASMA THAT IS FREE OR VIRTUALLY FREE OF CELLULAR BLOOD SPECIES

(75) Inventors: Jean Marie Mathias, Lillois (BE); Agneta Blom, Wauthie-Braine (BE); Luc Mespreuve, De Bruges (BE); Daniel Vandendaul, Lens (BE); Jean-Marc Payrat, Nivelles (BE)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/540,935

(22) Filed: Mar. 31, 2000

Related U.S. Application Data

(63) Continuation-in-part of application No. 09/082,946, filed on May 21, 1998, now Pat. No. 6,267,745.

(51) Int. Cl.⁷ .......................... A61M 1/14; A61M 35/00; B01D 36/02; B01D 29/00
(52) U.S. Cl. ....................... 422/44; 604/6.03; 604/6.09; 604/6.16; 604/406; 210/323.1; 210/348; 210/500.1; 210/505
(58) Field of Search ............... 604/4.01, 5.01–5.04, 604/6.01–6.05, 6.08, 6.09, 6.15, 6.16, 28, 45, 500, 506, 507, 257, 258, 262, 317, 326–27, 403, 405–6, 408, 411–16, 903; 422/1, 22, 24, 40–44; 210/634, 639, 641, 435–37, 503, 644, 649–51, 767, 781, 782, 789, 252, 255, 257.1–257.2, 294, 295, 323.1, 334, 348, 472, 500.1, 505

(56) References Cited

U.S. PATENT DOCUMENTS

| | | | |
|---|---|---|---|
| 3,058,799 A | 10/1962 | Rowles, Jr. | |
| 4,786,286 A | 11/1988 | Cerney et al. | |
| 4,790,815 A | 12/1988 | Balteau et al. | |
| 5,100,564 A | * 3/1992 | Pall et al. | 210/295 |
| 5,128,048 A | 7/1992 | Stewart | |
| 5,167,656 A | 12/1992 | Lynn | |
| 5,217,627 A | * 6/1993 | Pall et al. | 210/257.1 |
| 5,269,946 A | 12/1993 | Goldhaber et al. | |
| 5,283,033 A | 2/1994 | Dodrill | |
| 5,445,629 A | 8/1995 | Debrauwere et al. | |
| 5,451,321 A | 9/1995 | Matkovich | |
| 5,472,621 A | 12/1995 | Matkovich | |
| 5,514,106 A | 5/1996 | D'Silva | |
| 5,601,730 A | 2/1997 | Page et al. | |
| 5,616,254 A | 4/1997 | Pall et al. | |
| 5,695,489 A | 12/1997 | Japuntich | |
| 5,738,796 A | 4/1998 | Bormann et al. | |
| 5,804,079 A | 9/1998 | Brown | |
| 5,804,280 A | * 9/1998 | Pall et al. | 156/155 |
| 5,836,934 A | 11/1998 | Beshel | |
| 5,928,214 A | 7/1999 | Rubinstein et al. | |
| 5,935,092 A | * 8/1999 | Sun et al. | 210/496 |
| 5,941,866 A | 8/1999 | Niedospial, Jr. | |
| 6,051,147 A | 4/2000 | Bischof | |
| 6,190,855 B1 | * 2/2001 | Herman et al. | 422/44 |
| 6,267,745 B1 | 7/2001 | Mathias et al. | |

* cited by examiner

Primary Examiner—Angela D. Sykes
Assistant Examiner—Patricia Bianco
(74) Attorney, Agent, or Firm—Daniel D. Ryan; Michael Mayo

(57) ABSTRACT

Systems and methods treat plasma by separating targeted blood cell species such as red blood cells and platelets from the plasma by filtration through hydrophilic polyvinylidene fluoride (PVDF) membranes.

10 Claims, 10 Drawing Sheets

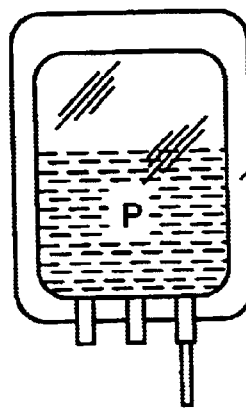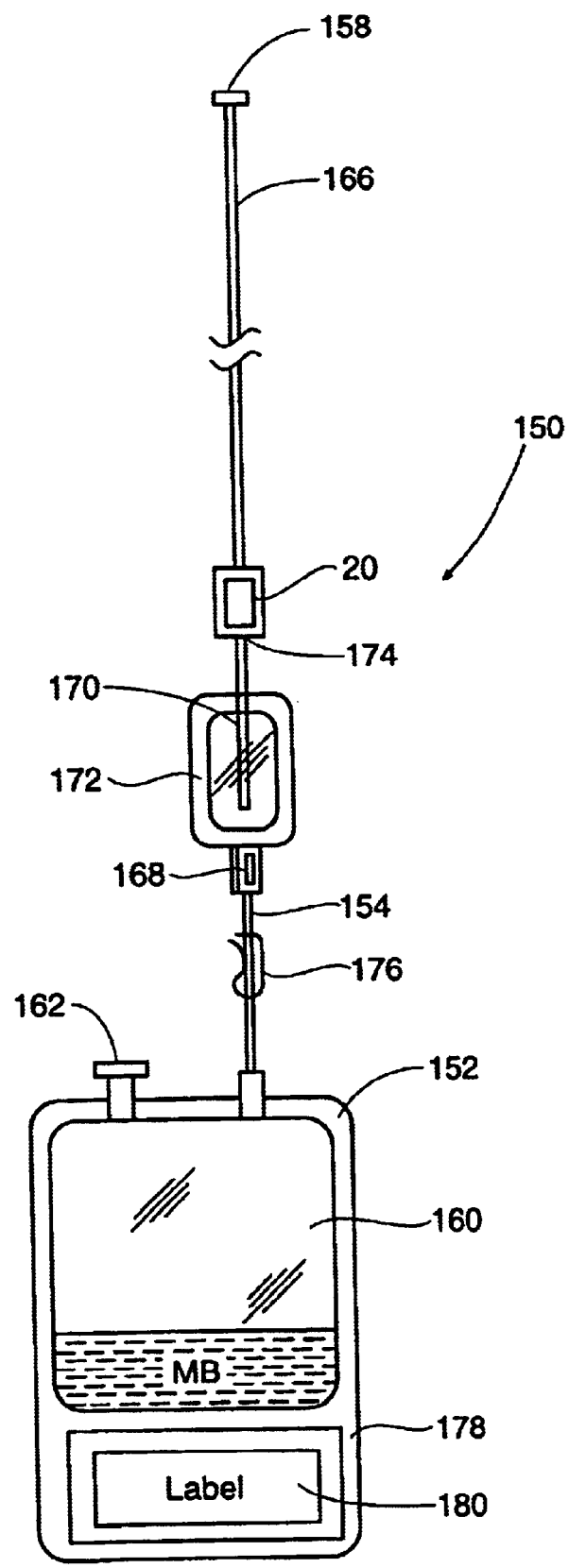
Fig. 9

SYSTEMS AND METHODS FOR COLLECTING PLASMA THAT IS FREE OR VIRTUALLY FREE OF CELLULAR BLOOD SPECIES

RELATED APPLICATION

This application is a continuation-in-part of co-pending U.S. patent application Ser. No. 09/082,946, filed May 21, 1998, and entitled "Confined Air Tube Methods for Handling Air in Closed Blood Processing Systems" (now U.S. Pat. No. 6,267,745), which is incorporated herein by reference.

FIELD OF THE INVENTION

The invention generally relates to the processing of whole blood and its components for storage, fractionation, and transfusion.

BACKGROUND OF THE INVENTION

With the coming of blood component therapy, most whole blood collected today is separated into its clinically proven components for storage and administration. The clinically proven components of whole blood include, e.g., red blood cells, which can be used to treat chronic anemia; plasma, which can be used as a blood volume expander or which can be fractionated to obtain Clotting Factor VIII-rich cryoprecipitate for the treatment of hemophilia; and concentrations of platelets, used to control thrombocytopenic bleeding.

Along with the growing demand for these blood components, there is also a growing expectation for purity of the blood product. For example, it is believed beneficial that plasma used for transfusion or fractionation be as free as possible of cellular blood species, such as leukocytes, red blood cells, platelets. For example, European Council Guidelines dictate that fresh frozen plasma should contain less than $6.0 \times 10^9$ residual red blood cells per liter, less than $0.1 \times 10^9$ residual leukocytes per liter, and less than $50 \times 10^9$ residual platelets per liter. There is therefore a growing demand for blood processing and storage systems that can treat plasma in a way that removes virtually all cellular blood species.

As another example, the use of photodynamic therapy has been suggested as a way to eradicate infectious agents from collected blood and its components. Still, not all biological contaminants are carried free within the blood where they can be readily coupled to photoactive agents. Some biological contaminants are entrained on or within blood cell species that the plasma carries. It is therefore desirable to remove these blood cell species from plasma for this reason.

SUMMARY OF THE INVENTION

The invention provides systems and methods for harvesting plasma that is free or virtually free of cellular blood species.

The systems and methods use tubing adapted to be coupled to a source of plasma. A filter is located in the tubing to separate targeted cellular blood species, such as red blood cells and platelets, from plasma that is conveyed from the source. The filter includes first and second hydrophilic polyvinylidene fluoride (PVDF) membranes having pores sized to remove these targeted cellular blood species from plasma by exclusion.

In one embodiment, the filter includes a prefilter layer that also removes aggregates larger than these targeted cellular blood species from plasma.

In one embodiment, the pores of the first PVDF membrane are larger than the pores of the second PVDF membrane. For example, the pores of the first PVDF membrane are about 1.0 $\mu$m in size, and the pores of the second PVDF membrane are about 0.65 $\mu$m in size.

In one embodiment, the first PVDF membrane has a porosity that is characterized by a water bubble point of between about 8.5 psi and 13 psi. In this embodiment, the second PVDF membrane has a porosity that is characterized by a water bubble point of between about 15.5 psi and 20.6 psi.

In one embodiment, the filter includes a flexible housing enclosing the first and second PVDF membranes.

In one embodiment, the filter includes a mesh layer in a downstream flow direction from the first and second PVDF membranes.

Other features and advantages of the invention will be pointed out in, or will be apparent from, the drawings, specification and claims that follow.

Description of the Drawings

FIG. 9 is a form of a manual blood processing system for collecting and inactivating virus in plasma, the system having a filter that removes blood cell species from the plasma prior to viral inactivation.

Figure 1:
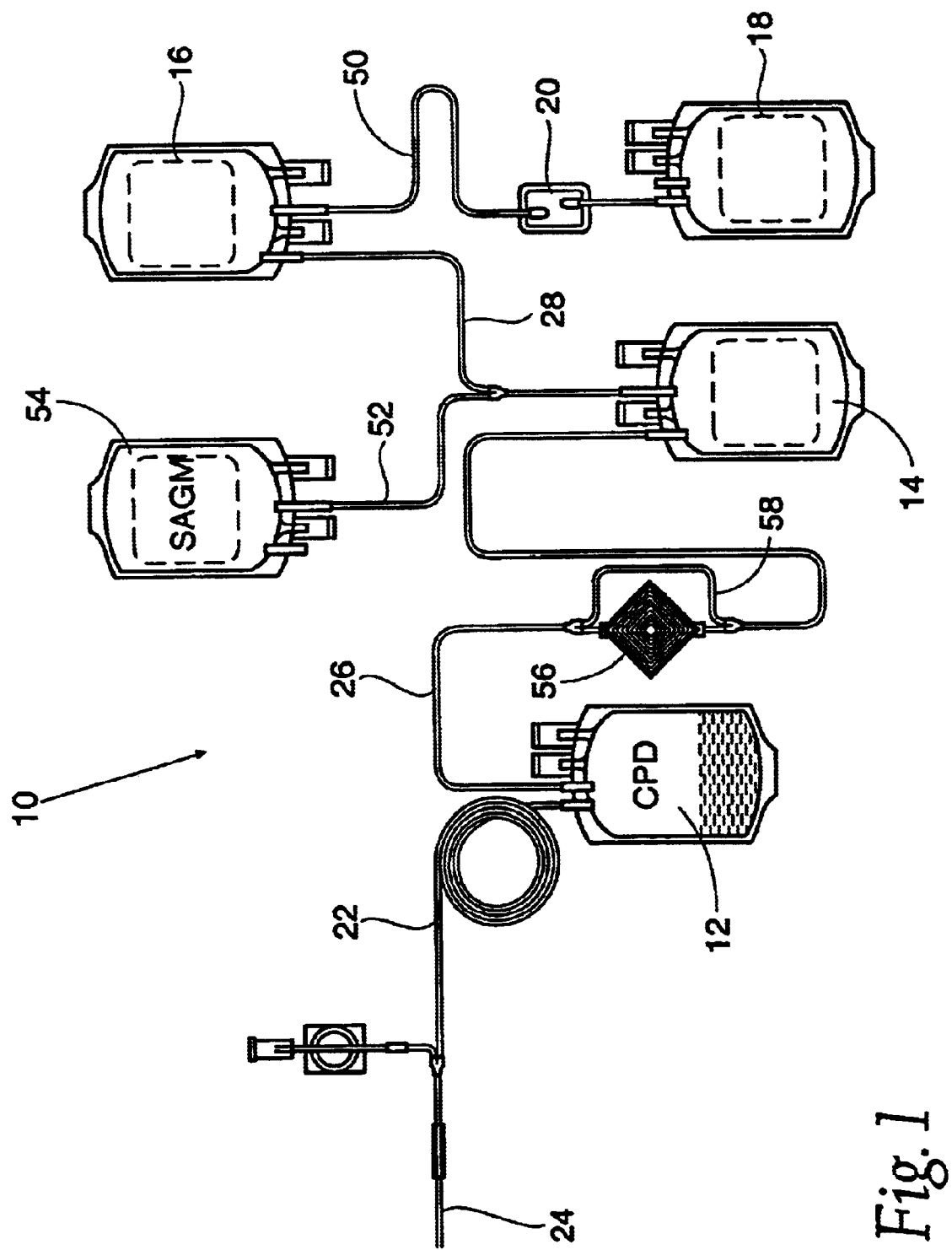
FIG. 1 is one form of a manual blood processing and storage system that includes a filter that removes blood cell species from plasma prior to storage.

The invention is not limited to the details of the construction and the arrangements of parts set forth in the following description or shown in the drawings. The invention can be practiced in other embodiments and in various other ways. The terminology and phrases are used for description and should not be regarded as limiting.

DESCRIPTION OF THE PREFERRED EMBODIMENTS

FIG. 1 shows a blood collection and storage system 10. The system 10 is intended, during use, to process a unit of whole blood into desired blood components for long term storage and transfusion. In the illustrated embodiment, the blood components targeted for collection comprise leukocyte-reduced red blood cells (with platelets) and plasma that is free or virtually free of cellular blood species, such as red blood cells, platelets, and leukocytes. The blood collection and storage system 10, once sterilized, constitutes a sterile, "closed" system, as judged by the applicable standards. The system 10 is intended to be a disposable, single use item.

The system 10 includes a blood collection container 12, a blood processing container 14, a plasma collection container 16, and a plasma storage container 18. Donor tubing 22, carrying a phlebotomy needle 24, is integrally attached to the whole blood collection container 12. First transfer tubing 26 integrally couples the blood collection container 12 to the blood processing container 14. Second transfer tubing 28 integrally couples the plasma collection container 16 to the blood processing container 14. Third transfer tubing 50 integrally couples the plasma storage container 18 to the plasma collection container 16.

Fourth transfer tubing 52 integrally couples an auxilliary container 54 to the second transfer tubing 28. The container 54 holds a red blood cell additive solution (e.g., SAGM), which is ultimately added to red blood cells collected in the system 10, as will be described later.

The containers and tubing associated with the processing system 10 can all be made from conventional approved, flexible, medical grade plastic materials, such as polyvinyl chloride plasticized with di-2-ethylhexyl-phthalate (PVC-DEHP). The containers are formed using conventional heat sealing technologies, e g., radio frequency (RF) heat sealing.

The system 10 is manipulated in conventional ways. Whole blood is collected through the donor tubing 22 in the blood collection container 12. A suitable blood anticoagulant (e.g., CPD) is carried in the blood collection container 12 for mixing with the collected whole blood.

After collection, the donor is disconnected. The donor tubing 22 is sealed and severed, and the anticoagulated whole blood is expressed through the first transfer tubing 26 into the blood processing container 14.

A first filter 56 is coupled in-line with the first transfer tubing 26. The filter 56 includes a medium that is selected to remove leukocytes from whole blood during its transit to the blood processing container 14. The filtration medium can, for example, be made from a fibrous material, such as melt blown or spun bonded synthetic fibers (e.g., nylon or polyester or polypropylene), semi-synthetic fibers, regenerated fibers, or inorganic fibers. The fibrous medium removes leukocytes by depth filtration.

Following filtration, residual air is vented from the blood processing container 14 through branch tubing 58, bypassing the filter 56, and into the blood collection container 12. The first transfer tubing 26 is then sealed and severed near the blood processing container 14.

The blood processing container 14, together with the still integrally attached downstream containers and tubing, are placed into a conventional blood centrifuge. In the centrifuge, the whole blood is centrifugally separated into red blood cells and blood cell-poor plasma. Since the system is intended to harvest plasma that is virtually free of blood cells, the rate of rotation is selected (employing a so-called "hard spin") to separate a majority of the platelets out of the plasma, along with the red blood cells. As a result, a majority of the platelets reside with the red blood cells, providing blood cell-poor plasma.

Following centrifugal separation, the blood cell-poor plasma is expressed from the blood processing container 14 into the plasma collection container 16. The second transfer tubing 28 is then sealed and severed close to the plasma collection container 16.

The red blood cell additive solution can now be transferred from the auxillary container 54 and mixed with the red blood cells (and platelets) remaining in the blood processing container 14. The second transfer tubing 28 is then sealed and severed close to the blood processing container 14. The red blood cells can be stored in the presence of the additive solution in conventional fashion in the blood processing container 14.

Blood cell-poor plasma is transferred from the plasma collection container 16 through the third transfer tubing 50 into the plasma storage container 18. A second filter 20 is coupled in-line with the third transfer tubing 50. The filter 20 includes a medium that is selected to remove all or virtually all residual red blood cells and platelets from the plasma (and which, due to the larger size of leukocytes, incidently will remove any residual leukocytes as well).

The third transfer tubing 50 is sealed and severed close to the plasma storage container 18. The virtually blood cell-free plasma can be stored in conventional fashion in the plasma storage container 18.

Figure 2:
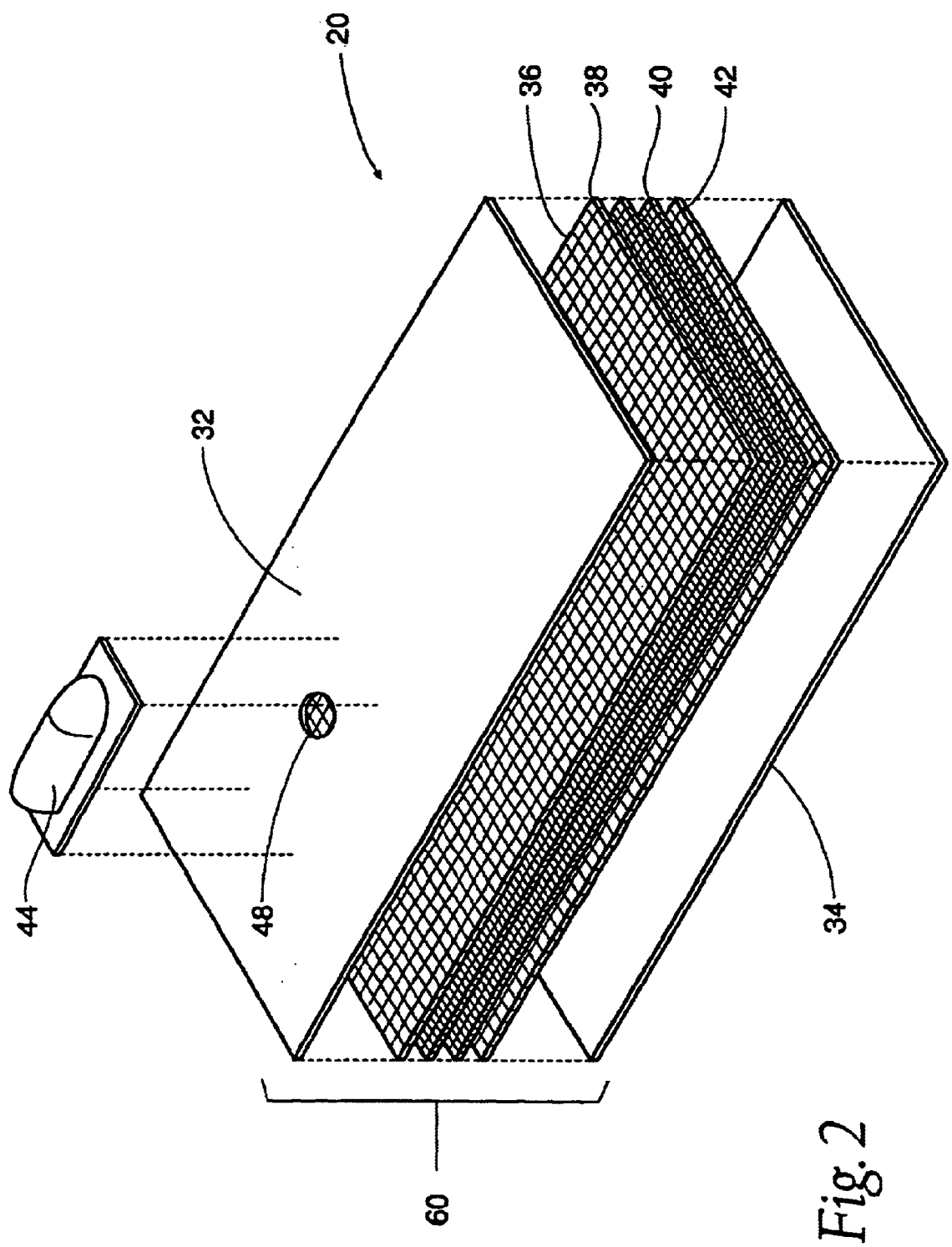
FIG. 2 is an exploded perspective view of the filter shown in FIG. 1.
Figure 3:
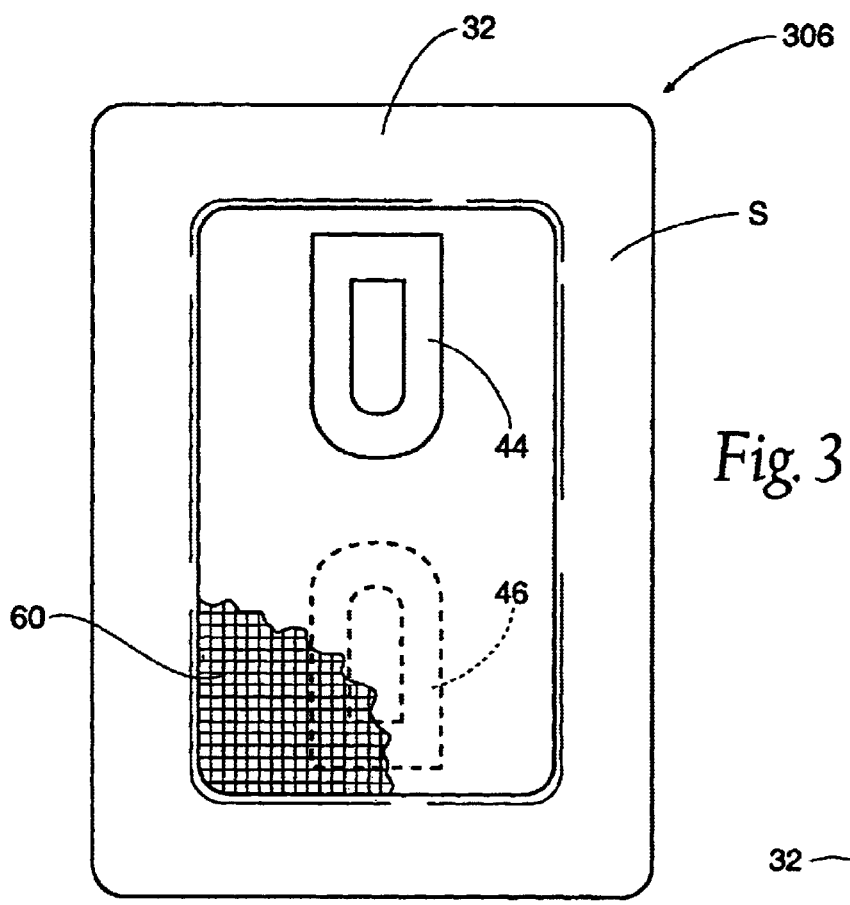
FIG. 3 is an assembled top plane view of the filter shown in FIG. 2.
Figure 4:
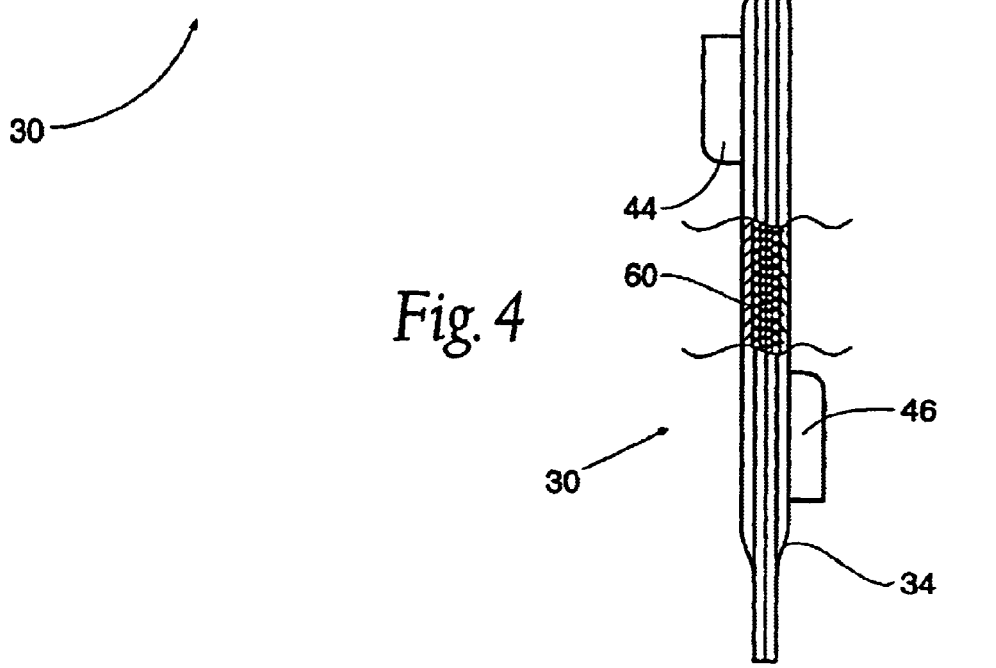
FIG. 4 is an assembled side elevation view of the filter shown in FIG. 2.

As FIGS. 3 and 4 show, the filter media 60 of the second filter 20 is enclosed within a filter housing 30. In the illustrated embodiment (see FIG. 2), the filter housing 30 comprises first and second sheets 32 and 34 of flexible, medical grade plastic material, such as polyvinyl chloride plasticized with di-2-ethylhexyl-phthalate (PVC-DEHP). A peripheral seal S, formed using conventional radio frequency heat sealing technology, joins the sheets 32 and 34 about the filter media. Other medical grade plastic materials can be used that are not PVC and/or are DEHP-free, provided that the material heats and flows when exposed to radio frequency energy.

The filter housing 30 could, alternatively,. comprise a rigid medical grade plastic material. However, use of flexible materials for the housing 30 better protects the tubing and containers in contact with the housing 30, from damage, particular when undergoing centrifugation.

The pore size of the filter media 60 of the second filter 20 is tailored to remove by exclusion the red blood cell and platelet species of blood cells typically found in plasma.

The composition of the media 60 can vary. For examples, hydrophilic membranes made from nylon, acrylic copolymers, polysulfone, polyvinylidene fluoride, mixed cellulose esters, and cellulose ester can be used to remove red blood cells and platelets by exclusion. Non-hydrophilic membranes can also be treated to serve as a membrane for the filter media 60. Material selection takes into account customer preferences, performance objectives, and manufacturing requirements, including sterilization techniques.

In the illustrated and preferred embodiment, (see FIG. 2), four layers 36, 38, 40, and 42 make up the filter media 60. The four layers 36, 38, 40, and 42 are arranged, one on top of the other, in the order of blood flow through the filter 20.

The first layer 36 comprises a prefilter material. The prefilter layer 36 serves to remove fibrin clots and other large size aggregates from the plasma, but may also retain cellular blood species by affinity. The composition of the prefilter layer 36 can vary and can comprise, e.g., fibers of glass or polyester. In the illustrated embodiment, the prefilter layer 36 comprises a borosilicate microfiber glass material with an acrylic binder resin. This material is commercially available from Millipore, under the product designation AP15 or AP20. The AP15 material is preferred, as it is less porous than the AP20 material and has been observed to provide better flow rates than AP20 material. For best flow rate results, the glass fiber prefilter layer 36 should be oriented with the gross surface facing in the upstream flow direction and the fine surface facing in the downstream flow direction.

The second and third filter media layers 38 and 40 preferably possess pore sizes which are approximately tenfold smaller than the size of leukocytes, and which decrease in the direction of flow. Due to their pore size, the second and third filter media layers 38 and 40 remove red blood cells and platelets (and incidently also leukocytes) by exclusion. In the illustrated embodiment, the second and third layers 38 and 40 comprise hydrophilic polyvinylidene fluoride (PVDF) membranes.

In a preferred embodiment, the PVDF material of the second filter media layer 38 has an average pore size of about 1.0 μm and a porosity sufficient to sustain an adequate flow of plasma through the filter 20, without plugging, which can be characterized by a bubble point (derived using water) in a range between about 8.5 psi and about 13 psi. This PVDF material is commercially available from Millipore under the trade designation CVPPB hydrophilic DURAPORE™ Membrane.

In the preferred embodiment, the PVDF material of the third filter media layer 40 has a smaller average pore size of about 0.65 μm. The layer 40 also has a porosity sufficient to sustain an adequate flow of plasma through the filter 20, without plugging, which can be characterized by a bubble point (derived using water) in a range of about 15.5 to about 20.6 psi. This PVDF material is commercially available from Millipore under the trade designation DVPP hydrophilic DURAPORE™ Membrane.

The bottommost, fourth layer 42 comprises a mesh material made, e.g., from a polyester or polypropylene material. The mesh material of the fourth layer 42 provides mechanical support for the filter. The mesh material of the fourth layer 42 also prevents the PVDF material of the third filter media layer 40 from sticking, during use, to the PVC sheet 34 along the outlet of the filter. Alternatively, the fourth layer 42 could be substituted by a roughened finished surface on the internal side of the downstream sheet 34 of the housing 30.

The plasma filter 20 includes inlet and outlet ports 44 and 46. In the illustrated embodiment (see FIG. 2, 3, and 4), the ports 44 and 46 comprise separately molded parts that are heat sealed by radio frequency energy over a hole 48 formed in the sheets 32 and 34, preferably before the peripheral seal S is created. Alternatively, the ports 44 and 46 can comprise tubes made of medical grade plastic material, like PVC-DEHP. In this arrangement, the tubes are inserted and sealed to each sheet 32 and 34 in a separate assembly process before the peripheral seal S is formed, in the manner shown in Fischer et al. U.S. Pat. No. 5,507,904, which is incorporated herein by reference.

In use, the inlet port 44 conveys plasma into contact with the prefilter layer 36. The axis of the inlet port 44 is generally parallel to the plane of the layer 36.

The plasma flows through the prefilter layer 36 and through the second and third PVDF layers 38 and 40. There, removal of red blood cells and platelets (and, incidently, leukocytes) occurs by exclusion. The outlet port 46 conveys virtually blood cell free plasma from the second and third PVDF filter layers 38 and 40, through the mesh material 42.

EXAMPLE 1

Two filters 20 were constructed in the manner just described. One filter (F1) employed a prefilter layer 36 made from a Millipore AP20 material. The other filter (F2) employed a less porous prefilter layer 36 made from a Millipore AP15 material. Both filters F1 and F2 employed PVDF materials for the second and third layers 38 and.40.

Figure 5:
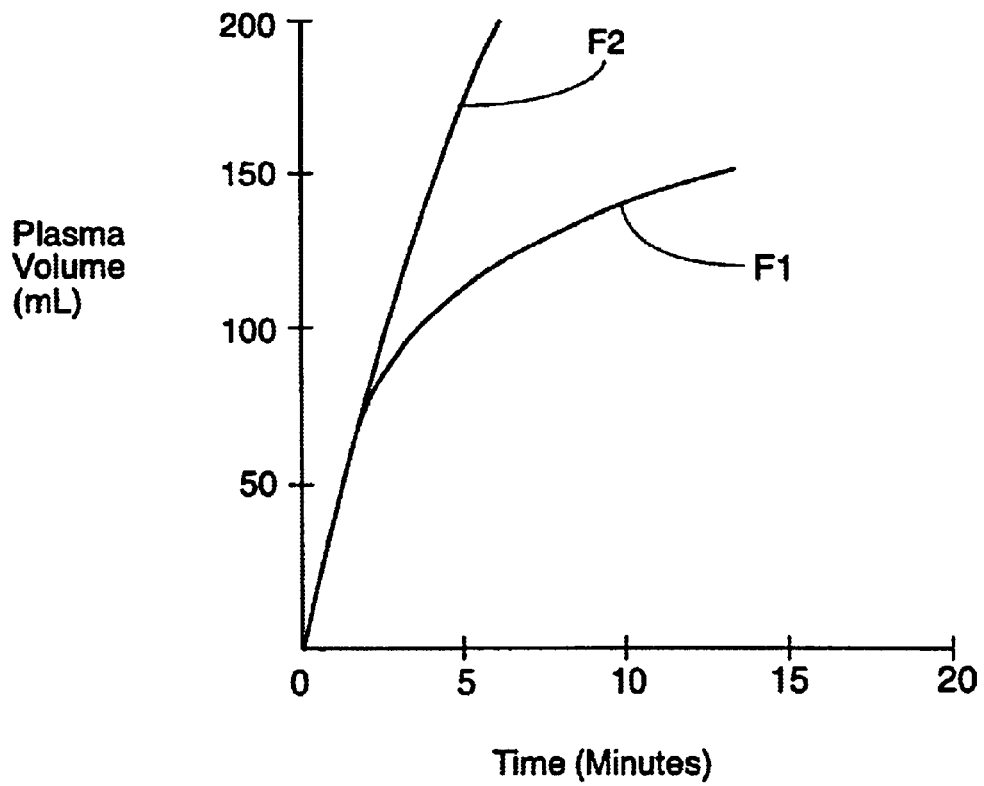
FIGS. 5 and 6 are graphs showing the rate of plasma flow through various filters that are made in accordance with the invention.

Human plasma was spiked with red blood cells to reach a concentration of $6.0 \times 10^9$ red blood cells per liter. The spiked plasma was conveyed through the filters F1 and F2 by gravity flow (head pressure of about 150 cm, corresponding to a transmembrane pressure of 0.15 kg/cm$^2$ (about 2 psi). FIG. 5 shows the plasma volume transiting the filters F1 and F2 over time.

FIG. 5 shows that both filters F1 and F2 sustained adequate plasma flow. Of the two, FIG. 5 shows that filter F2, with the less porous Millipore A15 material as the prefilter layer 36, sustained a better flow.

An automated counter was used to perform. prefiltration counting, while manual counting (Nageotte Chamber for leukocytes and Thoma Chamber for red blood cells and platelets) was used to determine postfiltration blood cell counts. For leukocytes, red blood cells, and platelets, the postfiltration counts were below the limits of detection for each counting method.

EXAMPLE 2

Similar filtration trials were conducted with individual filter layers. The trials show that the glass fiber prefilter layer 36 (made with Millipore A20 or A15 material) by itself excludes more than 90% of the available leukocytes and about 25% of the available red blood cells. The second PVDF layer 38 (1.0 μm) by itself excludes more than 95% of available leukocytes and about 80% of available red blood cells. The third PVDF layer 40 (0.65 μm) by itself excludes about 100% of available leukocytes and red blood cells. The combination of the glass fiber prefilter layer 36 and PVDF layers 38 and 40, as decribed, provide highly efficient, gradual exclusion of both leukocytes and red blood cells, without plugging.

EXAMPLE 3

Four filters F3, F4, F5, and F6 were constructed in the manner shown in FIG. 2. All filters employed a prefilter layer 36 made from a Millipore A15 material, as well as a mesh fourth layer 42, as described above. The porosity of the PVDF materials for the second and third layers 38 and 40 for the filters (characterized by a bubble point derived using water) varied as follows:

|    | Bubble Point for the Second Layer (1 μm PVDF Membrane) | Bubble Point for the Third Layer (0.65 μm PVDF Membrane) |
| --- | --- | --- |
| F3 | 8.5 | 15.6 |
| F4 | 13 | 15.6 |
| F5 | 8.5 | 20.6 |
| F6 | 13 | 20.6 |

Figure 6:
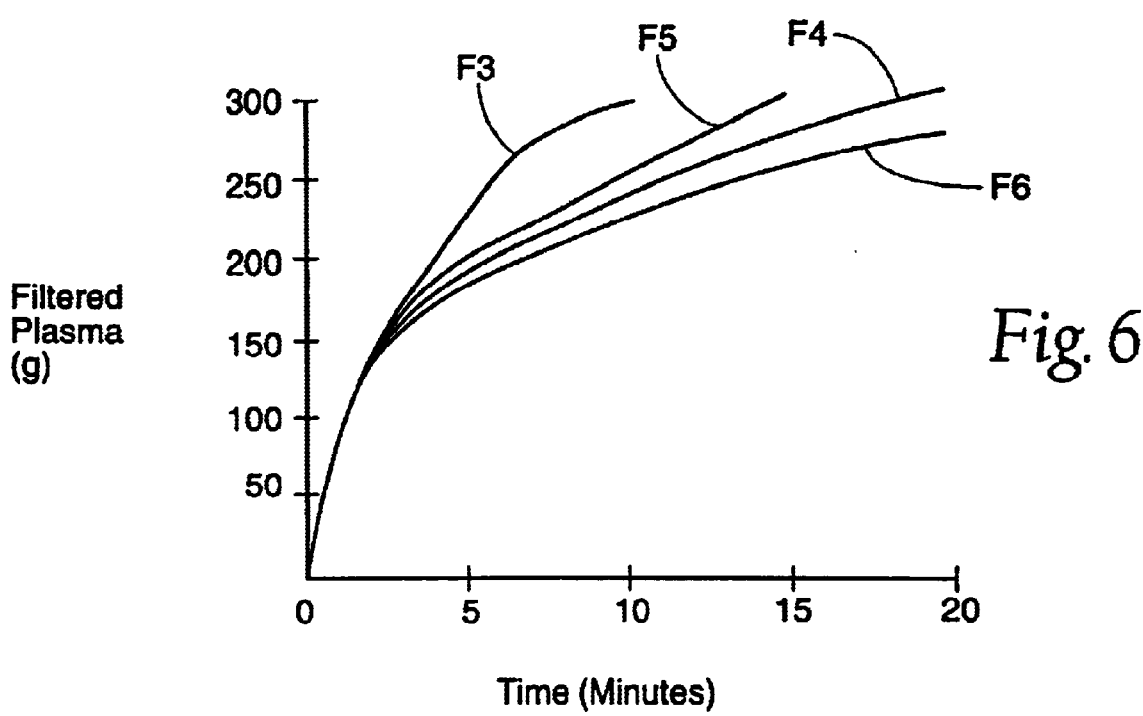

Human plasma was spiked with red blood cells to reach a concentration of $7.4 \times 10^9$ cells per liter. The spiked plasma was conveyed through the filters F3, F4, F5, and F6 by gravity flow. FIG. 6 shows the plasma volume transiting the filters F3, F4, F5, and F6 over time.

FIG. 6 shows that all filters F3, F4, F5, and F6 sustained adequate plasma flow. FIG. 6 shows that the porosity of the layers 38 and 40, as characterized by the bubble point, affects the flow characteristics of the filter. Best flow rates were achieved with filters F3 and F5, thereby prescribing the preferred bubble point ranges, defined above.

It has been observed that the triple layer membrane filter 306 described above provides plasma having a leukocyte level that is below the limit of detection of the two methods used for counting leukocytes, i.e., less than about 0.001 leukocytes using the flow cylometric method and less than 0.007 leukocytes per µL for the 30× concentrated Nageotte method. The actual residual level of leukocytes in the plasma after filtration by the filter 306 is estimated not to exceed an average theoretical level of 0.001 leukocyte per µL.

In addition to its use in the manual blood collection and storage system 10 shown in FIG. 1, the plasma filter 20 as just described can be used in diverse blood processing and storage systems where the harvesting of plasma virtually free of cellular blood species is desired.

Figure 7:
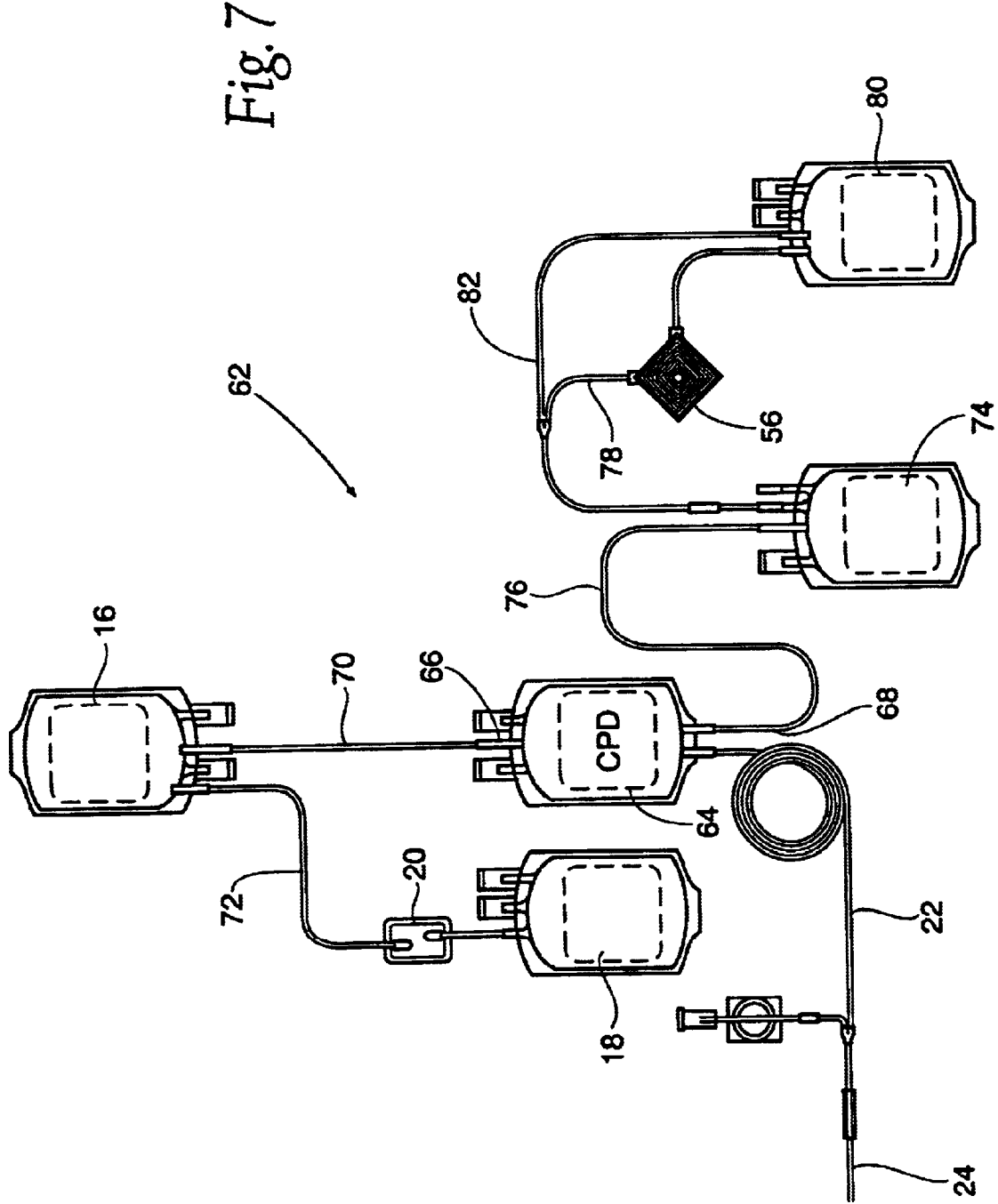
FIG. 7 is another form of a manual blood processing and storage system that includes a filter that removes blood cell species from plasma prior to storage.

For example, FIG. 7 shows a so-called "bottom and top" (or BAT) blood processing and storage system 62, which includes a whole bood collection container 64 having a top port 66 and a bottom port 68. The top port 66 is integrally coupled by top transfer tubing 70 to the plasma collection container 16. The plasma collection container 16 is, in turn, integrally connected by plasma transfer tubing 72 to the plasma storage container 18. In this arrangement, the plasma filter 20 is integrally coupled in-line with the plasma transfer tubing 72.

The bottom port 68 is integrally coupled to a red blood cell collection container 74 by bottom transfer tubing 76. The red blood cell collection container 74 can also contain a red blood cell additive solution, like SAGM, as already described. The red blood cell collection container 74 is integrally coupled by red blood cell transfer tubing 78 to a red blood cell storage container 80. A suitable filter 56 (as already described) for removing leukocytes from red blood cells is integrally coupled in-line in the red blood cell transfer tubing 78.

In use, whole blood is conveyed (via donor tubing 22 carrying a phlebotomy needle 24) into the whole blood collection container 64 (which contains a suitable anticoagulant, like CPD). The donor tubing 22 is sealed and severed. The whole blood collection container 64 (with still integrally attached containers and tubing) is placed inside a blood centrifuge. During centrifugation, the whole blood separates into a top layer of blood cell-poor plasma, a bottom layer of red blood cells, and an intermediate layer (called the buffy coat), in which mostly leukocytes and platelets reside.

Following separation in this manner, the whole blood collection container 64 is squeezed between two generally parallel plates of a plasma extractor, which is commercially available under the tradename OPTI-PRESS® System from Baxter Healthcare Corporation. The blood cell-poor plasma is expressed through the top port 66 into the plasma collection container 16, while the red blood cells are expressed from the bottom port 68 into the red blood cell collection container 74.

The location of the intermediate buffy coat layer is optically monitored, to retain the interface layer within the whole blood collection container 64. In this way, the leukocyte and platelet population of the red blood cells and plasma can be reduced. Also, the intermediate buffy coat layer can itself be later harvested for platelets after rinsing with a platelet additive solution followed by soft centrifugation.

Following transfer of blood cell-free plasma and red blood cells from the whole blood collection container 64, the top and bottom transfer tubing 70 and 76 are sealed and severed from the whole blood collection container 64. The blood cell-poor plasma is conveyed from the plasma collection container 16 to the plasma storage container 18 through the plasma filter 20. Filtered plasma, now virtually free of cellular blood species, is stored in conventional fashion in the plasma storage container 18. In like fashion, the red blood cells are conveyed from the red blood cell collection container 74 to the red blood cell storage-container through the filter 56. After filtration, residual air can be transferred from the red blood cell storage container 80 through branch tubing 82, bypassing the filter 56, into the red blood cell collection container 74. Filtered leuokodepleted red blood cells, virtually free of leukocytes, are stored in conventional fashion in the red blood cell storage container 80.

Figure 8:
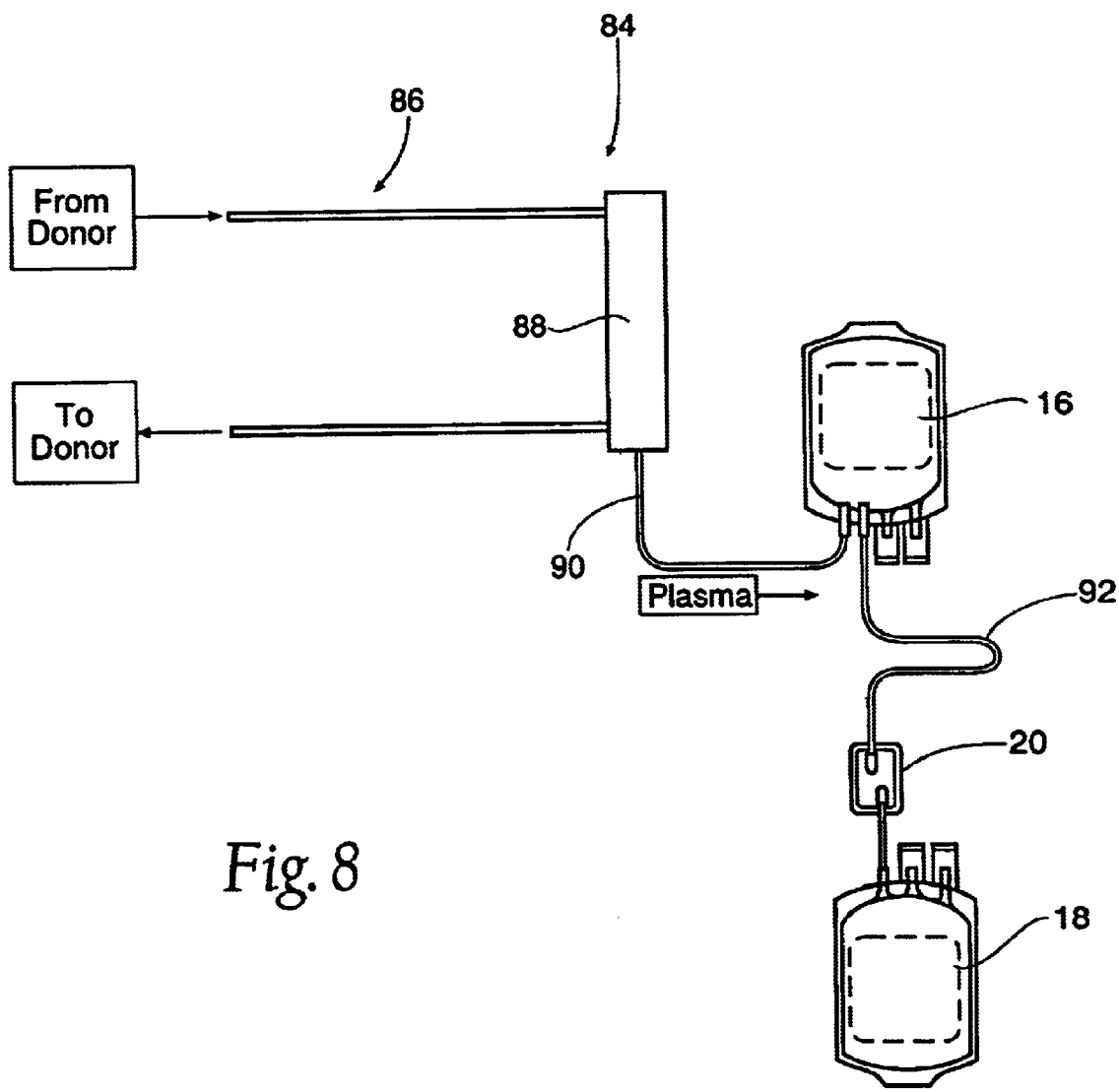
FIG. 8 is an apheresis plasma collection system that includes a filter that removes blood cell species from plasma being collected.

FIG. 8 shows an autopheresis system 84 for collecting plasma that is virtually free of blood cell species. The system 84 includes an extracorporeal circuit 86 that circulates whole blood from a donor through an on-line blood separation device 88, which separates blood cell-poor plasma from the whole blood. The remaining blood cells (comprising red blood cells, platelets, and leukocytes) are returned via the extracorporeal circuit 86 to the donor. The separation device 88 can comprise a conventional continuous or batch on-line centrifuge, or a spinning membrane separation device, which is commercially available under the tradename AUTOPHERESIS-C® System from Baxter Healthcare Corporation.

In this arrangement, the blood cell-poor plasma is conveyed through collection tubing 90 to the plasma collection container 16. The collection tubing 90 can be integrally connected to the blood separation device 88, or can be coupled by a suitable sterile connection technique to the blood separation device 88. For example, known sterile connection mechanisms like that shown in Spencer U.S. Pat. No. 4,412,835 can be used for connecting the container 16 to the transfer tubing 90. These mechanisms form a molten seal between tubing ends, which, once cooled, forms a sterile weld.

The plasma collection container 16 is integrally connected by plasma transfer tubing 92 to the plasma storage container 18. In this arrangement, the plasma filter 20 is integrally coupled in-line with the plasma transfer tubing 92. Following collection in the plasma collection container 16, the blood cell-poor plasma is conveyed through the filter 20 into the plasma storage container 18.

In the embodiments shown in FIGS. 1, 7, and 8, the blood cell-poor plasma is transfered into the plasma collection container 16, before passage through the filter 20 into the plasma storage container 18. It should be appreciated that, in alternative embodiments, blood cell-poor plasma can be transfered directly through the filter 20 into the plasma storage container 18, without passage through an intermediate plasma collection container 16.

FIG. 9 exemplifies another type of blood processing and storage system 150, which includes the plasma filter 20 that embodies features of the invention.

The system 150 shown in FIG. 9 is intended, during use, to assist in the removal of viral agents from plasma. The viral agents are either carried free within the plasma or are entrained on or within blood cell species (e.g., red blood cells, platelets, and leukocytes) that the plasma carries.

The system 150 includes a processing and storage container 152, which carries an integrally attached length of flexible transfer tubing 154. The container 152 is made of a material that is substantially transparent to the light energy applied during the photo activation process. The material for the container 152 is also adapted to withstand contemplated storage conditions for the plasma. In the illustrated embodiment, the container 152 is made of a plastic mixture of polyolefin materials, e.g., as made by Baxter Healthcare Corporation under the trademark PL-732® Plastic.

The processing and storage container 152 includes an interior chamber 160. The transfer tubing 154 communicates with the chamber 160 for conveying plasma into the chamber 160. The free end 166 of the tubing 154 in the system 150 is normally closed by a plug 158. During use, the free end 166 is coupled in a sterile fashion to a source of plasma P (shown as container 164 in FIG. 9).

A normally sealed outlet port 162 also communicates with the chamber 160. The port 162 is opened when it is time to remove plasma from the chamber 160.

The chamber 160 holds a liquid solution containing a photo active material, e.g., methylene blue (thereby designed MB in FIG. 9). The photo active solution MB mixes with the plasma P introduced into the chamber 160. The photo active material in the solution MB binds to extracellular viruses that plasma P introduced into the chamber 160 may carry. When exposed to light energy in a particular spectrum, the photo active material in the solution MB inactivates the nucleic acids of the bound viruses, rendering them nonviable.

The container 152 also includes a flap 178, which extends below the chamber 160. The flap 178 carries a printed label 180 having identifying indicia. The flap 178 keeps the label 180 away from the chamber 160, where it could block or impede the irradiating light.

A frangible cannula 168 normally closes liquid communication with the container 152 through the tubing 154. The transfer tubing 154 includes the integrally attached in-line plasma filter 20 upstream of the frangible cannula 168. The plasma filter 20 carries the filter medium 60 that removes from plasma blood cell species that do actually or potentially entrain viral agents.

To prevent the transfer tubing 154 (upstream of the frangible cannula 168) from collapsing and sticking together during heat sterilization, the system 150 includes a confined air tube 170. The air tube 170 is confined within an in-line air reservoir 172, which is located in the transfer tubing 154 between the filter 20 and the frangible cannula 168. The air tube 170 extends from the outlet 174 of the filter 20 a certain distance into the air reservoir 172. The air reservoir 172 comprises a peripherally sealed container made, e.g., of plasticized polyvinyl chloride material or another medical grade, heat sterilizable medical grade plastic material. Likewise, the air tube 170 is made from a heat sterilizable medical grade plastic material, like plasticized polyvinyl chloride.

The air tube 170 and the space created about it within the dry air reservoir 172, serve as the source of an incremental volume of air within the closed system 150. The presence of this incremental air volume obviates the need to introduce added helium or air during manufacture to prevent collapse and sticking of the transfer tubing 154.

A normally opened, external roller clamp or C-clamp 176 of conventional construction is also present between the air reservoir 172 and processing and storage container 152, downstream of the frangible cannula 168, for reasons to be explained later.

Figure 10:
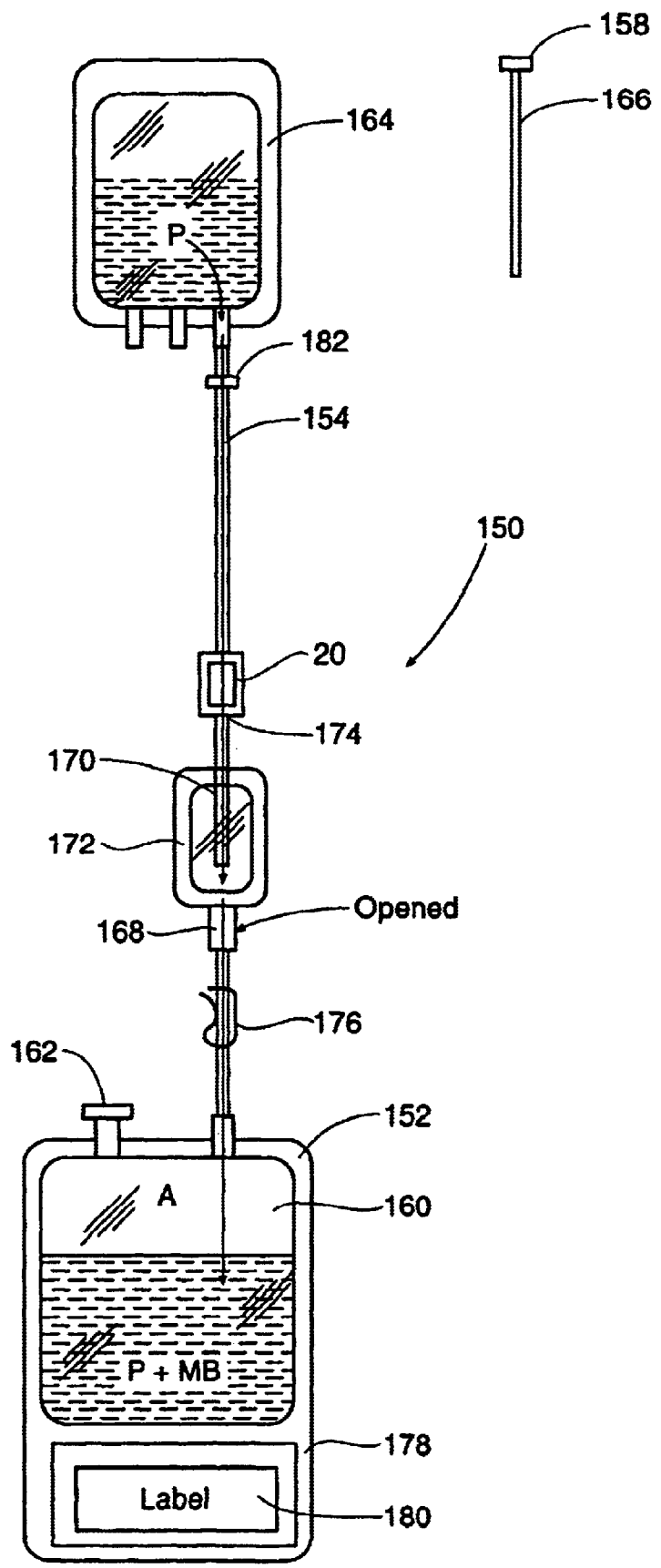
FIGS. 10, 11, and 12 are views of the system shown in FIG. 9, as it is manipulated during use.

In use (see FIG. 10), the container 164 holding the plasma P is connected in a sterile fashion to the transfer tubing 154 near the plug 158. The source container 164 can, for example, hold fresh plasma or plasma that has been frozen and thawed. The plasma is harvested by conventional blood banking procedures.

Known sterile connection mechanisms (not shown) like that shown in Spencer U.S. Pat. No. 4,412,835 can be used for connecting the container 164 to the transfer tubing 154. These mechanisms form a molten seal between tubing ends, which, once cooled, forms a sterile weld 182.

Once the sterile connection is made, the plugged tubing end 166 is discarded. The source S container 164 is suspended above the processing and storage container 152. The operator breaks the cannula 168 and leaves open the external C-clamp 176. The plasma P flows by gravity head pressure through the filter 20. The plasma, now virtually free of blood cell species, exits the filter 20 and drains into the chamber 160 of the container 152. The methylene blue photo active solution MB is mixed with the leukocyte-reduced plasma P within the container 152 by manual inversion.

Figure 11:
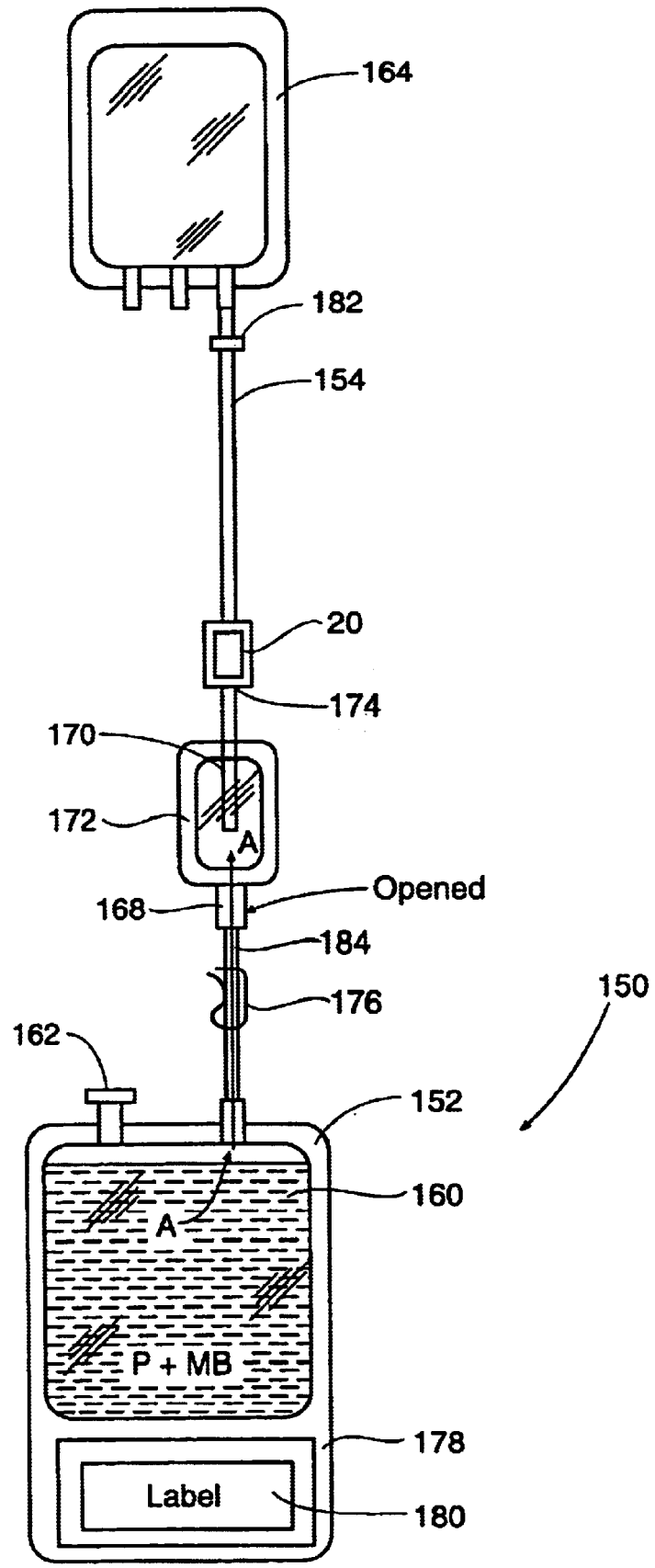

As FIG. 11 shows, after mixing plasma P and photo active material solution MB within the container chamber 160, the container 52 is held upright and squeezed. Air A is vented from the container 152 into the reservoir 172. The venting of air A also displaces residual plasma P, out of the transfer tubing 154 between the air reservoir 172 and the container 152. The container 152 is released to allow maximum drainage of plasma back into the container 152. Viruses in the residual plasma P, having never entered the container chamber 160 have not been exposed to the photo active material solution MB and therefore should be removed before undertaking the desired photo activation process by squeezing the container 152 for a second time.

As air venting proceeds, an amount of the mixture of photo active material solution MB and plasma P will enter the section 184 of the transfer tubing 154 between the reservoir 172 and the container 152. The mixture exposes this section of the transfer tubing 154 with the photo active material solution MB, to assure that viruses still occupying this section of the tubing 154 are exposed during air venting with the photo active material solution MB. This assures that all viruses present in the container 152 and adjacent tubing section 184 are exposed to the material solution MB, to thereby assure the desired virucidal effect during subsequent exposure to light irradiation.

Figure 12:
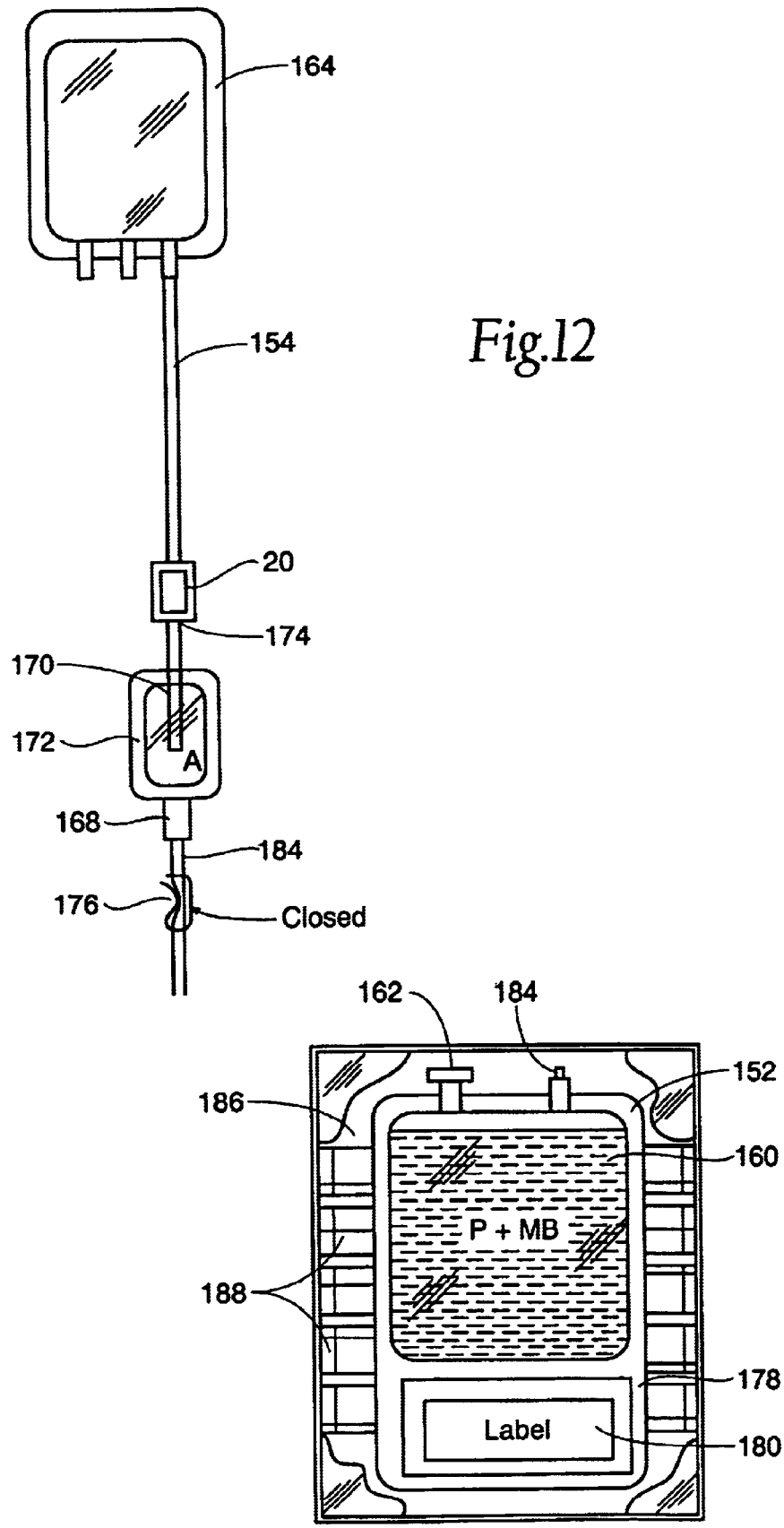

After air venting, the C-clamp 176 is closed to prevent air back-flow. The tubing section 184 is sealed closed using, for example, a dielectric tube sealer. As FIG. 12 shows, the remaining portion of the system 150 containing the filter 20 is removed and discarded. A remnant of the tubing 184 remains connected to the container 152.

The container 152 holding the methylene blue and virtually blood cell-free plasma, and carrying a remnant of the tubing section 184, is placed into a white light chamber 186. The chamber 186 comprises fluorescent lamps 188, which supply output in the visible range (400 to 700 nm) to both sides of the container 152. Alternatively, high pressure sodium lamps can be used. The light activates the methylene blue to release singlet oxygen, which inactivates viruses in the plasma.

After the illumination step, the virtually blood cell free plasma is frozen within the container 152 at less than −30° C. for storage using conventional blood bank practices. The plasma within the container 152 is thawed when fractionation or transfusion is required.

Features and advantages of the invention are forth in the following claims.

We claim:

1. A system for treating plasma comprising tubing adapted to be coupled to a source of plasma to convey plasma from the source, a filter in the tubing to separate aggregates and targeted cellular blood species including red blood cells and platelets from plasma conveyed from the source container, the filter including a prefilter that removes aggregates from plasma, the filter further including, arranged sequentially in a downstream flow direction from the prefilter, first and second hydrophilic polyvinylidene fluoride (PVDF) membranes having pores sized to remove the targeted cellular blood species from plasma by exclusion, the pores of the first PVDF membrane being about 1.0 m in average size and having a porosity that is characterized by a water bubble point of between about 8.5 psi and 13 psi, the pores of the second PVDF membrane being about 0.65 m in average size and having a porosity that is characterized by a water bubble point of between about 15.5 psi and 20.6 psi.

2. A system according to claim 1 and further including a transfer container coupled to the tubing to receive plasma after passage through the filter.

3. A system according to claim 2 further including a photoactive material in the transfer container.

4. A system according to claim 1 wherein the filter includes a flexible housing enclosing the prefilter layer and the first and second PVDF membranes.

5. A system according to claim 4 wherein the filter includes, enclosed within the flexible housing, a mesh layer arranged in a downstream flow direction from the first and second PVDF membranes.

6. A system according to claim 1 wherein the prefilter layer includes glass fiber.

7. A method for treating plasma comprising the steps of harvesting plasma from whole blood, and removing all or virtually all of red blood cells and platelets from the plasma by filtration through a prefilter that removes aggregates from plasma and, arranged sequentially in a downstream flow direction from the prefilter, porous first and second hydrophilic polyvinylidene fluoride (PVDF) membranes, the first PVDF membrane having pores about 1.0 $\mu$m in average size and having a porosity that is characterized by a water bubble point of between about 8.5 psi and 13 psi, the second PVDF membrane having pores about 0.65 $\mu$m in average size and having a porosity that is characterized by a water bubble point of between about 15.5 psi and 20.6 psi.

8. A method according to claim 7 wherein the plasma is harvested in a manual blood collection system.

9. A method according to claim 7 wherein the plasma is harvested in a blood separation device in an on-line extracorporeal circuit.

10. A method according to claim 7 further including the steps of adding to the plasma a photoactive material, and emitting radiation at a selected wavelength into the plasma to activate the photoactive material.

\* \* \* \* \*